United States Patent [19]

Sealfon et al.

[11] 4,447,232
[45] May 8, 1984

[54] SPRING-OPERATED LIQUID-DISPENSING DEVICE

[75] Inventors: Andrew Sealfon, Middletown; Carl Yurdin, Port Washington, both of N.Y.

[73] Assignee: Repro-Med Systems, Inc., Middletown, N.Y.

[21] Appl. No.: 380,564

[22] Filed: May 21, 1982

[51] Int. Cl.$^3$ .............................................. A61M 7/00
[52] U.S. Cl. .................................. 604/134; 604/214; 222/95
[58] Field of Search ................... 604/134, 214; 222/95, 222/103

[56] References Cited

U.S. PATENT DOCUMENTS

| | | | |
|---|---|---|---|
| 3,084,722 | 4/1963 | Klingerman | 222/103 X |
| 3,565,292 | 2/1971 | Jinotti | 604/134 X |
| 4,265,241 | 5/1981 | Portner et al. | 604/134 X |
| 4,280,637 | 7/1981 | Runciman | 222/95 X |

Primary Examiner—Stephen C. Pellegrino
Attorney, Agent, or Firm—Bauer & Amer

[57] ABSTRACT

A device, noteworthy by its compact construction, portability and use of a constant torque spring to dispense liquid under a uniform force, in which binding due to possible rotative movement in the slide that is powered by the torque spring is obviated, so that the slide tracks properly during liquid-dispensing service of the device, This is in contrast to torque spring-operated prior art devices in which special precautions were required to neutralize the turning movement unavoidably resulting when the torque spring assumed its characteristic helical coils during its functioning.

2 Claims, 6 Drawing Figures

U.S. Patent   May 8, 1984   4,447,232
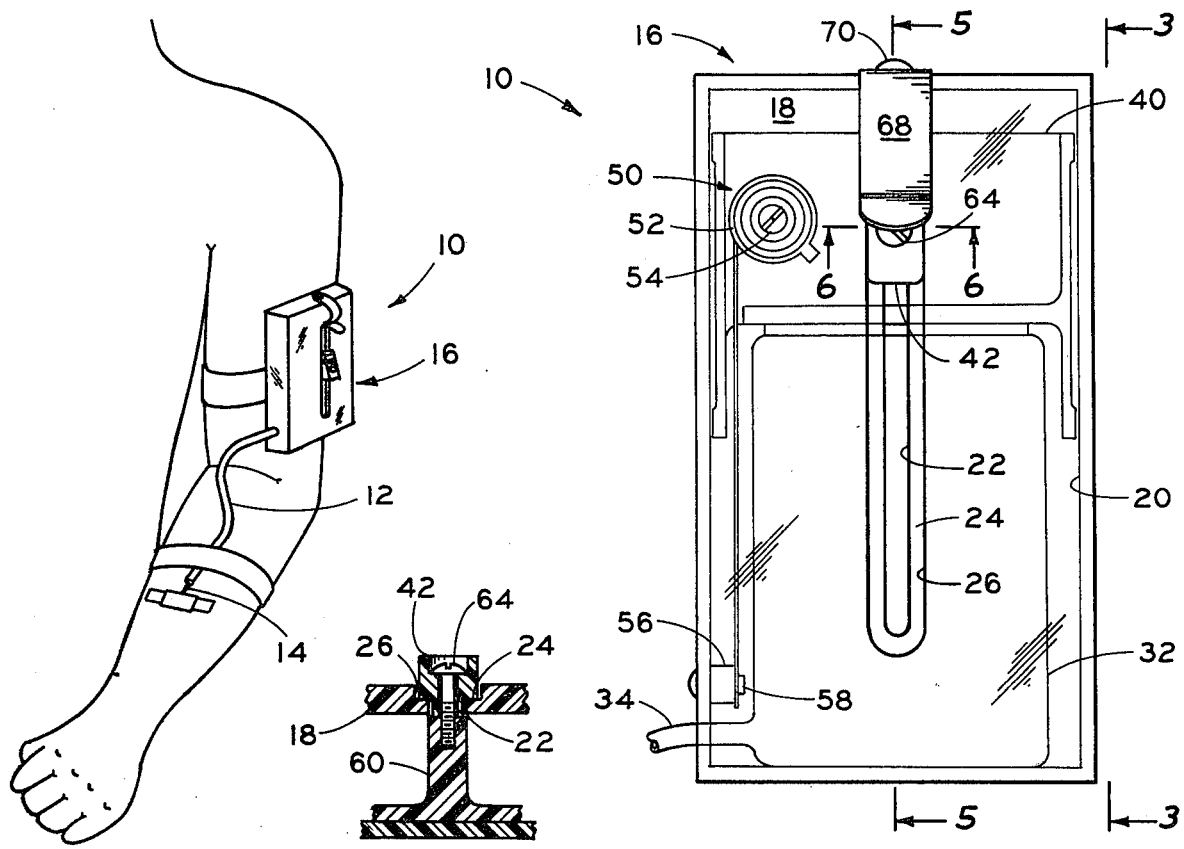
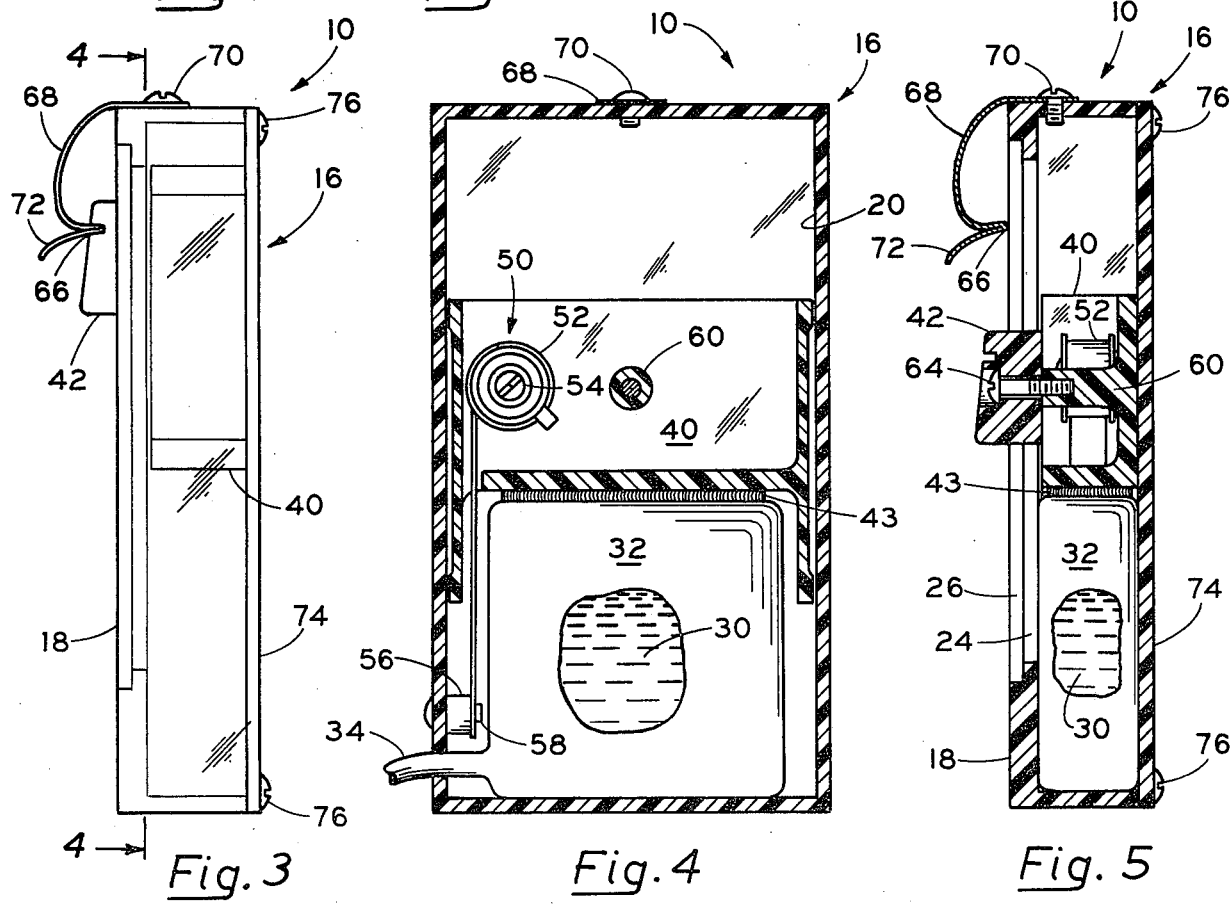
Fig. 1  Fig. 6  Fig. 2  Fig. 3  Fig. 4  Fig. 5

SPRING-OPERATED LIQUID-DISPENSING DEVICE

The present invention relates generally to improvements for a liquid-dispensing device operated by a constant or uniform force of a constant torque spring, said spring, as is well understood, being of the type that assumes a configuration of helical coils according to its built-in tendency, and more particularly relates to obviating the rotative tendency of said spring during operation of the within inventive device while maintaining the simplicity of the construction in the within inventive device, its portability and other noteworthy attributes as will become more apparent as the description proceeds.

Designed specifically for medical objectives, such as intravenous feeding or the dispensing of the evaporative fluid of the device of U.S. Pat. No. 4,253,464, although not necessarily limited to such end uses, the device hereof is of the general classification having an operational mode for which it has long been known is particularly suitable to be powered by a constant torque spring. However, a constant torque spring produces linear movement as might be appropriate for dispensing liquid from a collapsible bag by shortening its supply length, such as occurs when an end of the spring assumes the configuration or form of helical coils, and in this way can be made to push an operative member against a liquid-filled bag incident to forcing the liquid therefrom. Heretofore, however, the helical coils assumed by the spring unavoidably produced a rotative tendency in the bag-squeezing operative member, thus causing binding against walls or the like and otherwise adversely affecting the linear sliding movement thereof. The solution of using two springs and operatively arranging the turning tendencies in opposition to each other, does produce the desired neutralization, but at the expense of complicating the construction, adding weight, and introducing other complications.

Broadly, it is an object of the present invention to provide a medically-oriented liquid-dispensing device, efficiently powered by a constant torque spring overcoming the foregoing and other shortcomings of the prior art. Specifically, the within device uses a constant torque spring to apply a uniform pressure to dispense liquid, and achieves both linear tracking unaffected by the force feedback of the helical coils of the spring and convenient handling of the device, by use of noteworthy tracking structure embodied in the device, all as will be more particularly described herein.

A spring-operated device for dispensing a liquid for achieving a medical or similar objective demonstrating objects and advantages of the present invention includes a rectangular-shaped housing bounding an internal compartment having a top cover disposed in covering relation over said compartment. The cover has a centrally located slot orienated longitudinally thereof opening into the compartment, in which in practice there is disposed a source of liquid in a collapsible bag. Also operating in the compartment is a slide member disposed in pushing contact against the liquid-filled bag. A constant torque spring of the type adapted to assume the form of helical coils is operatively connected at one end to the slide member and at its opposite end to an end of the housing so as to urge the slide member through sliding movement through the compartment in response to the assumption of said helical coils at the spring end that is connected to the slide member. A significant structural feature is an upstanding leg on the slide member which is disposed in projected relation into the slot of said cover so as to be adapted to track along the slot during the sliding movement of the slide member. It has been found in practice that the tracking centrally along the cover by the slide member leg obviates any rotative tendency in the slide member as might be caused by a force feedback from the spring helical coils, and this correspondingly obviates any binding against the compartment walls by the slide member while it is urged by the spring through its power stroke.

The above brief description, as well as further objects, features, and advantages of the present invention, will be more fully appreciated by reference to the following detailed description of a presently preferred, but nonetheless illustrative embodiment in accordance with the present invention, when taken in conjunction with the accompanying drawings, wherein:

FIG. 1 is a perspective view illustrating a typical end use of the within device for intravenous feeding;

FIGS. 2-6 are more particularly concerned with illustrating the structural features of the device. In a preferred embodiment, the construction material of the device is a transparent plastic. Accordingly, FIG. 2 is a plan view in which internal structural features are visible through the transparent cover of the device;

FIG. 3 is a side elevational view as seen in the direction of the arrows 3—3 in FIG. 2 illustrating further structural details;

FIG. 4, like FIG. 2, is also a plan view, but taken along line 4—4 of FIG. 3 to illustrate additional internal structural features;

FIG. 5 is a sectional view taken along line 5—5 of FIG. 2 illustrating details of the upstanding leg of the slide member of the within device; and FIG. 6 is a partial sectional view, taken along line 6—6 of FIG. 2, illustrating still further structural details of said slide member upstanding leg.

Referring to the drawings, and particularly FIG. 1, the within inventive device, generally designated 10, is illustrated in a typical end use in which it is used for intravenous feeding. That is, and as will be explained in greater detail subsequently, the device 10 is noteworthy in that it is operated by a spring and is effective in dispensing liquid, which in the end use illustrated in FIG. 1 is an appropriate intravenous medicant through a tube 12 to an intravenous site 14. Consistent with achieving a medical or similar objective, it will also be understood that the device 10 is also appropriate to use as the fluid source 38 of the device 10 of U.S. Pat. No. 4,253,464, issued Mar. 3, 1981, entitled "Method and Device for Contributing to the Obviating of Male Infertility." The specific end uses are mentioned to highlight certain noteworthy operating requirements for the device 10, namely that it is capable of dispensing in a uniform fashion a liquid, and that it is spring-operated so that it is portable and therefore can be conveniently worn by the patient, such as on the patient's arm as illustrated in FIG. 1 when used for intravenous feeding, and on the patient's body when used for the medical objective of U.S. Pat. No. 4,253,464.

In a preferred embodiment, the construction material for the device 10 is any suitable clear or transparent plastic material. Using this construction material, the device includes a rectangular housing 16, consisting of the usual side, end and bottom walls and, warranting specific mention, a top panel or cover 18 which is disposed in any suitable manner in covering relation over an internal compartment 20 which is bounded by the housing 16, 18. A significant structural feature of the top cover 18 is a centrally located, longitudinally oriented slot 22 which opens into the compartment 20 and which in cross-section, as illustrated in the sectional view of FIGS. 5, 6 has two walls, 24 and 26, along opposite sides to cooperate in forming a shoulder for a tracking function which will soon be described.

Disposed within the compartment 20 is a source of liquid, identified by the reference number 30, which will be understood to be appropriate for the medical objective that is intended to be accomplished, said liquid being contained within a collapsible bag 32 which has outlet 34 which, in the illustrated end use, is connected to an intravenous tube and needle 12.

A next significant component of the device 10 consists of a slide member 40 which is disposed for sliding movement also in the compartment 20 and, more particularly, in pushing contact against the collapsible bag 32. To achieve an actual interconnected relationship between the bag 32 and front of the slide member 40, use may be made of cooperating Velcro patches at the interface of the contacting surfaces of the bag and slide member, as at 43.

To power slide member 40 in sliding movement from an initial starting position, as at the top of FIG. 2, to a final position which, of course, would be to the bottom of FIG. 4, in which instance the fluid 30 would be forced out of the bag 32 through outlet 34, use is made of a constant torque spring, generally designated 50. The constant torque spring 50 is a well understood and commercially available component and therefore a detailed description thereof is not believed necessary for purposes of understanding the within invention. It suffices to note that spring 50 is of the type which exerts a constant or uniform force and has a natural tendency to assume the shape of helical coils, as indicated at 52. To permit this, slide member 40 includes a rotatably mounted core 54 on which one end of the spring 50 assumes the shape of helical coils 52, while the opposite end, as at 56, is stationarily connected adjacent an end of the housing 16 in any appropriate manner, such as by using the screw and clamp 58. That is, and in accordance with the well understood operational mode of the constant torque spring 50, the end not attached to the housing 16 is under a spring urgency and therefore assumes the form of helical coils 52 about the core 54 which shortens the supply length of the spring 50. Since the end 56 is connected at 58 to the housing 16, shortening in the spring 50 must in turn result in the slide member 40 being urged through sliding movement through the compartment 20. Since the slide member 40 is in pushing contact against the bag 32, this of course results in the desired dispensing of the liquid therefrom under the constant or uniform force of the spring 50.

The significant problem overcome in the construction of the within device 10 which heretofore prevented the use of liquid dispensing devices operated by constant torque springs is that the helical coils 52 formed in said spring has a tendency to urge the member to which it is attached, in this instance the slide member 40, in rotative movement about the rotation axis of the core 54. To neutralize this according to prior art practice would require the use of two springs 50, each one along one of the sides of the slide and thereby providing a symmetrical construction to the device. In other words, the use of two springs 50 would presumably provide two tendencies for rotative movement and since these could be operatively arranged in opposition to each other, they would neutralize each other. While the aforesaid would prevent binding which might occur due to any rotative movement in the slide member 14 during its sliding traverse in the compartment 20, the use of two springs 50 is not desirable since there would be exerted more spring bias than is necessary, and the weight contributed to the device 10 by the two springs might also be excessive and contribute to discomfort in wearing the device, which it will be recalled is directly on the patient. Also, two springs would have to be balanced, and would contribute other undesirable operating parameters which are unavoidable when more than one torque spring is used.

The within inventive solution which permits the use of only one constant torque spring 50 on any selected side in off-centered relation on the slide member 40 will now be described in detail. Essentially, the solution is provided by having an upstanding leg 60 as an integral part of the slide member 40, the upper portion of said leg projecting into and contacting the lower wall of slot 22 of the top cover 18. Connected to the projecting end of the leg 60 is an operative tracking member 42, the connection being made by as simple an expedient as a screw 64. As is perhaps best illustrated in FIGS. 2, 5 and 6, the tracking member 62 is readily confined to track along the slot 22 by the bottom corners thereof being guided along the shoulders formed by the cooperating walls 24 and 26 which are part of the slot construction of the top cover 18.

At this point in the description it should be noted that the tracking member 62 is advantageously provided with a transverse slot 66 for receiving an unattached end of a spring clip 68, of appropriate springy construction material, which is attached at its opposite end to the rear wall of the housing 16, as by the screw 70. As a result, and as is perhaps best illustrated in FIG. 3, the clip spring 68 can effectively engage the tracking member 62 and in this manner hold the slide member 40 in its ready position to the top of the device 10. When it is desired, however, to start the liquid-dispensing function of the device 10, a finger grip 72 of the clip spring 68 is adapted to be engaged and lifted out of slot 66 thereby releasing the slide member 40 for movement under the spring urgency of the single spring 50 against the liquid-filled bag 32.

In some end uses, the condition for maintaining sterile the liquid being dispensed is consistent with making use of the same plastic bag 32. In this instance an appropriate vacuum tube would be connected to the extending tube 34 and in withdrawing the slide member 40 back to its starting position another supply of fluid would, of course, be drawn into the bag 32. During this time, of course, the slide member 40 is eased into its starting position and held in place by the resilient clip 68. Repetitious use of the same bag 32 might be particularly applicable for the end use contemplated for the device 10 in the referred-to U.S. Pat. No. 4,253,464. If a fresh bag 32 is necessary, bottom plate 74 is unscrewed at 76 to permit this.

A latitude of modification, change and substitution is intended in the foregoing disclosure, and in some instances some features of the invention will be employed without a corresponding use of other features. Accordingly, it is appropriate that the appended claims be construed broadly and in manner consistent with the spirit and scope of the invention herein.

What is claimed is:

1. A spring-operated device for dispensing a liquid for achieving a medical or similar objective, said device comprising a rectangular-shaped housing bounding an internal compartment having a top cover disposed in covering relation over said compartment, said cover having a centrally located slot oriented longitudinally thereof opening into said compartment, a source of liquid in a collapsible bag disposed in said compartment, a slide member disposed in said compartment in pushing contact against said liquid-filled bag, a single constant torque spring of the type adapted to assume the form of helical coils disposed along one side of said compartment and operatively connected at one end to said slide member and at said opposite end to an end of said housing so as to urge said slide member through sliding movement through said compartment in response to said assumption of said helical coils at said end connected to said slide member, an upstanding leg on said slide member in projected relation into said slot of said cover so as to be adapted to track along said slot during said sliding movement of said slide member, whereby said tracking centrally along said cover by said slide member leg obviates any rotative tendency in said slide member as might be caused by said spring helical coils and correspondingly obviates any binding against said compartment walls by said slide member, a tracking member disposed for tracking movement in said slot of said cover attached to said projecting end of said upstanding leg of said slide member, and a clip means connected to said housing for selectively engaging said tracking member preparatory to commencing the liquid-dispensing service of said device.

2. A spring-operated liquid-dispensing device as claimed in claim 1 wherein a detachable connection is established between the contacting surfaces of the liquid-filled bag and said slide member, to thereby provide an option of replacing or reusing said bag in subsequent use of said device.

* * * * *